US008084407B2

(12) United States Patent
Soffin et al.

(10) Patent No.: US 8,084,407 B2
(45) Date of Patent: *Dec. 27, 2011

(54) MILD, STRUCTURED, MULTIPHASE PERSONAL CLEANSING COMPOSITIONS COMPRISING DENSITY MODIFIERS

(75) Inventors: Daniel Jacob Soffin, Fairfield, OH (US); Scott William Syfert, Ft. Mitchell, KY (US); Karl Shiqing Wei, Mason, OH (US); Edward Dewey Smith, III, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 202 days.

This patent is subject to a terminal disclaimer.

(21) Appl. No.: 11/400,634

(22) Filed: Apr. 7, 2006

(65) Prior Publication Data

US 2006/0252662 A1 Nov. 9, 2006

Related U.S. Application Data

(60) Provisional application No. 60/670,785, filed on Apr. 13, 2005, provisional application No. 60/680,114, filed on May 12, 2005, provisional application No. 60/680,149, filed on May 12, 2005.

(51) Int. Cl.
*C11D 17/00* (2006.01)

(52) U.S. Cl. ........ 510/130; 510/136; 510/156; 510/424; 510/426; 510/428; 510/475; 424/70.14

(58) Field of Classification Search ................ None
See application file for complete search history.

(56) References Cited

U.S. PATENT DOCUMENTS

| 2,020,454 A | 11/1935 | Bisbee et al. |
|---|---|---|
| 2,658,072 A | 11/1953 | Kosmin |
| 2,986,271 A | 5/1961 | Forrer |
| 3,455,440 A | 7/1969 | West |
| 3,479,429 A | 11/1969 | Morshauser et al. |
| 3,533,955 A | 10/1970 | Pader et al. |
| 3,542,256 A | 11/1970 | Waterman |
| 3,618,757 A | 11/1971 | Funkhouser |
| 3,800,998 A | 4/1974 | Gask |
| 3,850,365 A | 11/1974 | Dietrich |
| 3,899,076 A | 8/1975 | Florian |
| 3,929,678 A | 12/1975 | Laughlin et al. |
| 3,937,811 A | 2/1976 | Papantoniou et al. |
| 3,951,679 A | 4/1976 | Bernhard et al. |
| 3,980,767 A | 9/1976 | Chown et al. |
| 4,159,028 A | 6/1979 | Barker et al. |
| 4,263,363 A | 4/1981 | Buck et al. |
| 4,335,103 A | 6/1982 | Barker et al. |
| 4,379,753 A | 4/1983 | Bolich, Jr. |
| 4,425,322 A | 1/1984 | Harvey et al. |
| 4,518,578 A | 5/1985 | Hayes et al. |
| D292,879 S | 11/1987 | Smith |
| 4,966,205 A | 10/1990 | Tanaka |
| 4,980,155 A | 12/1990 | Shah et al. |
| 5,002,680 A | 3/1991 | Schmidt et al. |
| 5,059,414 A | 10/1991 | Dallal et al. |
| 5,223,315 A | 6/1993 | Katsura et al. |
| 5,228,189 A | 7/1993 | Driller et al. |
| 5,228,912 A | 7/1993 | Herget et al. |
| 5,304,334 A | 4/1994 | Lahanas et al. |
| 5,393,450 A | 2/1995 | Shana'a et al. |
| 5,455,035 A | 10/1995 | Guerrero et al. |
| 5,487,168 A | 1/1996 | Geiner et al. |
| 5,540,853 A | 7/1996 | Trinh et al. |
| 5,556,628 A | 9/1996 | Derian et al. |
| 5,578,299 A | 11/1996 | Starch |
| 5,612,307 A | 3/1997 | Chambers et al. |
| 5,632,420 A | 5/1997 | Lohrman et al. |
| 5,635,171 A | 6/1997 | Nadaud et al. |
| 5,661,189 A | 8/1997 | Grievson et al. |
| 5,687,779 A | 11/1997 | Andersson et al. |
| 5,716,920 A | 2/1998 | Glenn et al. |
| 5,851,978 A | 12/1998 | Shana'a |
| 5,873,494 A | 2/1999 | Dallas, Jr. |
| 5,914,117 A * | 6/1999 | Lavaud ................ 424/401 |
| 5,925,603 A | 7/1999 | D'Angelo |
| 5,929,019 A | 7/1999 | Puvvada et al. |
| 5,947,335 A | 9/1999 | Milio et al. |
| 5,952,286 A | 9/1999 | Puvvada et al. |
| 5,954,213 A | 9/1999 | Gerhart et al. |
| 5,965,500 A | 10/1999 | Puvvada |
| 5,965,501 A | 10/1999 | Rattinger et al. |
| 5,972,361 A | 10/1999 | Fowler et al. |
| D426,158 S | 6/2000 | Flurer et al. |
| 6,174,845 B1 | 1/2001 | Rattinger et al. |
| 6,176,391 B1 | 1/2001 | Rehkemper et al. |
| 6,176,395 B1 | 1/2001 | Abbott et al. |
| 6,190,648 B1 | 2/2001 | Kouzu et al. |
| 6,194,364 B1 | 2/2001 | Glenn, Jr. |
| D438,460 S | 3/2001 | Hammond |
| D439,165 S | 3/2001 | Erckelbout et al. |
| 6,213,166 B1 | 4/2001 | Thibiant et al. |
| D441,645 S | 5/2001 | Longhurst |
| 6,232,496 B1 | 5/2001 | Carr et al. |
| 6,245,323 B1 | 6/2001 | Christie et al. |
| 6,245,344 B1 | 6/2001 | Thibiant et al. |
| 6,268,322 B1 | 7/2001 | St. Lewis et al. |
| 6,306,806 B1 | 10/2001 | St. Lewis et al. |
| 6,335,312 B1 | 1/2002 | Coffindaffer et al. |

(Continued)

FOREIGN PATENT DOCUMENTS

CA 2246316 6/1998

(Continued)

OTHER PUBLICATIONS

International Search Report, PCT/US2006/012401, dated Aug. 7, 2006, 6 pages.

(Continued)

*Primary Examiner* — Necholus Ogden, Jr.

(57) ABSTRACT

A mild, multiphase cleansing composition is described that includes a structured surfactant component has a first density; a benefit component that has a second density; and a density modifier; wherein the first density differs from the second density by less than 0.15 g/cm³; the structured surfactant component includes at least one surfactant and provides a Total Lather Volume of at least about 600 ml.

22 Claims, No Drawings

U.S. PATENT DOCUMENTS

| | | |
|---|---|---|
| 6,340,723 B1 | 1/2002 | Nita et al. |
| D455,655 S | 4/2002 | Bunce |
| 6,367,519 B2 | 4/2002 | Thibiant |
| 6,383,999 B1 | 5/2002 | Coyle et al. |
| 6,385,992 B1 | 5/2002 | Flore, Jr. |
| 6,394,323 B2 | 5/2002 | McClean et al. |
| 6,419,783 B1 | 7/2002 | Rainey et al. |
| 6,426,326 B1 | 7/2002 | Mitra et al. |
| 6,429,177 B1 | 8/2002 | Salmon et al. |
| 6,495,498 B2 | 12/2002 | Niemiec et al. |
| 6,506,391 B1 | 1/2003 | Biatry |
| 6,517,939 B1 | 2/2003 | Ramin et al. |
| 6,521,216 B1 | 2/2003 | Glandorf et al. |
| 6,534,456 B2 | 3/2003 | Hayward et al. |
| 6,534,457 B2 | 3/2003 | Mitra |
| 6,534,458 B1 | 3/2003 | Hayward et al. |
| 6,547,063 B1 | 4/2003 | Zaveri et al. |
| 6,555,509 B2 | 4/2003 | Abbas et al. |
| 6,564,978 B1 | 5/2003 | Safian et al. |
| 6,574,985 B2 | 6/2003 | Fiore, Jr. |
| 6,589,509 B2 | 7/2003 | Keller et al. |
| 6,652,134 B2 | 11/2003 | Lloyd |
| 6,663,855 B2 | 12/2003 | Frechet et al. |
| 6,673,371 B2 | 1/2004 | Brown et al. |
| 6,673,755 B2 | 1/2004 | Wei et al. |
| D486,395 S | 2/2004 | Lovell et al. |
| D486,398 S | 2/2004 | Lovell et al. |
| 6,691,394 B1 | 2/2004 | McClean |
| 6,695,510 B1 | 2/2004 | Look et al. |
| 6,924,256 B2 | 8/2005 | Massaro et al. |
| 7,143,893 B2 | 12/2006 | Kelly |
| 7,144,542 B2 | 12/2006 | Holzer et al. |
| 7,273,837 B2 | 9/2007 | Boutique et al. |
| 7,524,807 B2 | 4/2009 | Clapp et al. |
| 7,537,819 B2 | 5/2009 | Hendricks |
| 7,666,825 B2 | 2/2010 | Wagner et al. |
| 2001/0036467 A1 | 11/2001 | Thibiant et al. |
| 2002/0004468 A1 | 1/2002 | Hodge et al. |
| 2002/0010110 A1 | 1/2002 | Hayward et al. |
| 2003/0003069 A1 | 1/2003 | Carson et al. |
| 2003/0152540 A1 | 8/2003 | Putman et al. |
| 2003/0161852 A1 | 8/2003 | Miller et al. |
| 2003/0180246 A1 | 9/2003 | Frantz et al. |
| 2003/0222100 A1 | 12/2003 | Husband et al. |
| 2004/0048757 A1 | 3/2004 | Zhang et al. |
| 2004/0048758 A1 | 3/2004 | Zhang et al. |
| 2004/0057920 A1 | 3/2004 | Focht et al. |
| 2004/0091445 A1 | 5/2004 | Dykstra et al. |
| 2004/0092415 A1* | 5/2004 | Focht et al. ................ 510/130 |
| 2004/0105827 A1 | 6/2004 | Grimm et al. |
| 2004/0146475 A1 | 7/2004 | Peffly et al. |
| 2004/0158940 A1 | 8/2004 | Wells et al. |
| 2004/0180020 A1 | 9/2004 | Manelski et al. |
| 2004/0219119 A1 | 11/2004 | Wei et al. |
| 2004/0223929 A1 | 11/2004 | Clapp et al. |
| 2004/0223991 A1 | 11/2004 | Wei et al. |
| 2004/0223992 A1 | 11/2004 | Clapp et al. |
| 2004/0232023 A1 | 11/2004 | Bansal et al. |
| 2004/0235693 A1 | 11/2004 | Wei et al. |
| 2004/0242706 A1 | 12/2004 | Wiersema et al. |
| 2004/0248748 A1* | 12/2004 | Wei et al. .................. 510/130 |
| 2004/0248749 A1 | 12/2004 | Mitra et al. |
| 2005/0003975 A1 | 1/2005 | Browne et al. |
| 2005/0020468 A1 | 1/2005 | Frantz et al. |
| 2005/0100570 A1 | 5/2005 | Wei et al. |
| 2005/0139574 A1 | 6/2005 | Simone et al. |
| 2005/0143269 A1 | 6/2005 | Wei et al. |
| 2005/0192187 A1 | 9/2005 | Wagner et al. |
| 2005/0192188 A1 | 9/2005 | Wagner et al. |
| 2005/0192189 A1* | 9/2005 | Wagner et al. ............. 510/130 |
| 2005/0238680 A1 | 10/2005 | Stella et al. |
| 2005/0249758 A1 | 11/2005 | Di Puccio Pagano |
| 2005/0269372 A1 | 12/2005 | Smith |
| 2005/0276768 A1 | 12/2005 | Wei et al. |
| 2006/0002880 A1 | 1/2006 | Peffly et al. |
| 2006/0008438 A1 | 1/2006 | Velarde et al. |
| 2006/0042184 A1 | 4/2006 | Wagner et al. |
| 2006/0079419 A1 | 4/2006 | Wagner et al. |
| 2006/0079420 A1 | 4/2006 | Wagner et al. |
| 2006/0094628 A1 | 5/2006 | Wei et al. |
| 2006/0210505 A1 | 9/2006 | Clapp et al. |
| 2006/0276357 A1 | 12/2006 | Smith, III et al. |
| 2007/0141001 A1 | 6/2007 | Clapp et al. |
| 2007/0187274 A1 | 8/2007 | Dalea et al. |
| 2007/0248562 A1 | 10/2007 | Berry et al. |
| 2007/0280976 A1 | 12/2007 | Taylor et al. |
| 2010/0020937 A1 | 8/2010 | Wei et al. |

FOREIGN PATENT DOCUMENTS

| | | |
|---|---|---|
| DE | 196 50 952 A | 6/1998 |
| DE | 198 54 086 A | 5/2000 |
| EP | 0 078138 A2 | 5/1983 |
| EP | 0 331617 B | 4/1992 |
| EP | 1 108421 A2 | 6/2001 |
| EP | 1 005849 B1 | 9/2001 |
| EP | 1 064918 B1 | 9/2002 |
| EP | 0 907345 B1 | 5/2003 |
| GB | 1277324 A | 6/1972 |
| JP | 2000229817 A | 8/2000 |
| JP | 2002-128639 A | 5/2002 |
| JP | 2002-138010 A | 5/2002 |
| WO | WO 90/13283 A1 | 11/1990 |
| WO | WO 94/10973 A1 | 5/1994 |
| WO | WO 97/17938 A1 | 5/1997 |
| WO | WO 98/27193 A1 | 6/1998 |
| WO | WO 99/38489 A1 | 8/1999 |
| WO | WO 99/38491 A1 | 8/1999 |
| WO | WO 00/75240 A1 | 12/2000 |
| WO | WO 01/01931 A1 | 1/2001 |
| WO | WO 01/23517 A1 | 4/2001 |
| WO | WO 01/70193 A2 | 9/2001 |
| WO | WO 01/70926 A1 | 9/2001 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO2004/050055 * | 6/2004 |
| WO | WO 2004/050055 * | 6/2004 |
| WO | WO 2004/050055 A1 | 6/2004 |
| WO | WO2004/096162 * | 11/2004 |
| WO | WO 2005/016304 A1 | 2/2005 |
| WO | WO 2005/067875 A1 | 7/2005 |
| WO | WO2005/084614 * | 9/2005 |
| WO | WO 2006/042176 A1 | 4/2006 |
| WO | WO 2006/042184 A1 | 4/2006 |

OTHER PUBLICATIONS

C.D. Vaughan, "Solubility, Effects in Product, in Package, Penetration and Preservation," Cosmetic and Toiletries, vol. 103, Oct. 1988.

CTFA International Cosmetic Ingredient Dictionary, Fourth Edition, 1991, pp. 12 and 80.

J. Caelles et al., "Anionic and Cationic Compounds in Mixed Systems, "Cosmetics & Toiletries, vol. 106, Apr. 1991. pp. 49-54.

C.J. van Oss, "Coacervation, Complex-Coacervation and Flocculation," J. Dispersion Science and Technology, vol. 9 (5, 6), 1988-89, p. 561-573.

D.J. Burgess, "Practical Analysis of Complex Coacervate Systems," J. of Colloid Anti Interface Science, vol. 140, No. 1, Nov. 1990, pp. 227-238.

KOBO Brochure, "Treated Pigments" (May 2000).

* cited by examiner

MILD, STRUCTURED, MULTIPHASE PERSONAL CLEANSING COMPOSITIONS COMPRISING DENSITY MODIFIERS

CROSS REFERENCE TO RELATED APPLICATIONS

This application claims the benefit of U.S. Provisional application Ser. No. 60/670,785 filed on Apr. 13, 2005 and U.S. Provisional application Ser. No. 60/680,114 filed on May 12, 2005 and U.S. Provisional application Ser. No. 60/680,149 filed on May 12, 2005.

FIELD OF THE INVENTION

The present invention relates to a mild, structured, multiphase, personal cleansing composition that comprises a density modifier wherein the first density of the structured surfactant component differs from the second density of the benefit component by less than 0.15 g/cm.$^3$

BACKGROUND OF THE INVENTION

Personal cleansing compositions that attempt to provide skin-conditioning benefits are known. Many of these compositions are aqueous systems comprising an emulsified conditioning oil or other similar materials in combination with a lathering surfactant. Although these products provide both conditioning and cleansing benefits, it is often difficult to formulate a product that deposits sufficient amount of skin conditioning agents on skin during use. In order to combat emulsification of the skin conditioning agents by the cleansing surfactant, large amounts of the skin conditioning agent are added to the compositions. However, this introduces another problem associated with these dual cleansing and conditioning products. Raising the level of skin conditioning agent in order to achieve increased deposition negatively affects product stability.

It is known that dispersions and emulsions in personal cleansing compositions that comprise structured surfactants exhibit buoyant forces due to the difference in density between the continuous structured surfactant component, and the benefit component. For example, when the benefit component comprises a hydrophobic material such as a triglyceride or a hydrocarbon material, the density of the dispersed phase is about 0.9 gm/cm$^3$, whereas the density of the continuous structured surfactant component is about 1.0 gm/cm$^3$. When the buoyant force of a benefit component exceeds the local value of the yield stress of the continuous structured surfactant component, the droplet can rise through the continuous phase in a process called creaming. Given a sufficient amount of creaming, exacerbated by coalescence of the benefit component, phase separation can occur as the product becomes unstable, e.g., during shipping and extended storage on a store shelf.

Accordingly, the need still remains for a multiphase, blended personal cleansing composition that provides both cleansing and improved skin conditioning benefits which remains for a personal cleansing composition comprising two phases in physical contact that remain stable for long periods of time.

SUMMARY OF THE INVENTION

The present invention relates to a mild, multiphase cleansing composition that comprises a structured surfactant component has a first density; a benefit component that has a second density and a density modifier; wherein the first density differs from the second density by less than 0.15 g/cm$^3$; the structured surfactant component comprises at least one surfactant and provides a Total Lather Volume of at least about 600 ml.

The present invention also relates to a mild, multiphase cleansing composition that comprises a structured surfactant component that has a first density; a benefit component that has a second density; and a density modifier; wherein the first density differs from the second density by less than 0.15 g/cm$^3$; the surfactant comprises at least one surfactant and provides a Total Lather Volume of at least about 600 ml; wherein the mild, multiphase composition that comprises an opaque structured domain; wherein the opaque structured domain is lamellar phase.

The present invention also relates to a mild, structured, multiphase personal cleansing composition that comprises a structured surfactant component; a benefit component; and a density modifier; the structured surfactant component comprises at least one surfactant and provides a Total Lather Volume of at least about 600 ml; the mild, multiphase cleansing composition has a density of preferably less than about 0.97 g/cm$^3$.

The inventors believe that when the structured surfactant component comprises low density particles such that all parts of the structured composition are exposed to buoyant forces by the dispersed low density phase and the low density particles, creaming and phase separation are mitigated and the composition can be stabilized even under harsh conditions such as high temperature shipping and storage conditions. Preferably, a large number of low density particles are added so that all parts of the structured surfactant composition are exposed to buoyant forces.

The inventor believe that a multiphase personal cleansing composition containing both cleansing and benefit phases that are blended together can be formulated to provide improved cosmetics and skin feel during and after application while also providing excellent skin conditioning and cleansing benefits. The inventors believe that such a composition can be formulated with sufficiently high levels of benefit agents without compromising product lather performance and stability.

The inventors believe that personal cleansing compositions can be formulated with enhanced stability by density matching of the cleansing phase and the benefit phase and by incorporating density modifiers in the cleansing phase and/or the benefit phase.

DETAILED DESCRIPTION OF THE INVENTION

The term "ambient conditions" as used herein, refers to surrounding conditions at one (1) atmosphere of pressure, 50% relative humidity, and 25° C.

By the term "multi-phase" or "multi-phase" as used herein, is meant that the phases of the present compositions occupy separate but distinct physical spaces inside the package in which they are stored, but are in direct contact with one another (i.e., they are not separated by a barrier and they are not emulsified or mixed to any significant degree). In one preferred embodiment of the present invention, the "multi-phase" personal care compositions comprise at least two visually distinct phases which are present within the container as a visually distinct pattern. The pattern results from the combination of the "multi-phase" composition by a process herein described. The "patterns" or "patterned" include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. Preferably the pattern is selected from the group consisting of striped, geometric, marbled, and combinations thereof.

In a preferred embodiment, the striped pattern may be relatively uniform across the dimension of the package. Alternatively, the striped pattern may be uneven, i.e. wavy, or may be non-uniform in dimension. The striped pattern does not need to necessarily extend across the entire dimension of the package. The size of the stripes can be at least about 0.1 mm in width and 10 mm in length, preferably at least about 1 mm in width and at least 20 mm in length as measured from the package exterior. The phases may be various different colors, and/or include particles, glitter or pearlescent agents in at least one of the phases in order to offset its appearance from the other phase(s) present.

The term "multi-phase personal care composition" as used herein, refers to compositions intended for topical application to the skin or hair.

The term "surfactant component" as used herein means the total of all anionic, nonionic, amphoteric, zwitterionic and cationic surfactants in a phase. When calculations are based on the surfactant component, water and electrolyte are excluded from the calculations involving the surfactant component, since surfactants as manufactured typically are diluted and neutralized.

The term "structured," as used herein means having a rheology that confers stability on the multi-phase composition. The degree of structure is determined by characteristics determined by one or more of the following methods the Yield Stress Method, or the Zero Shear Viscosity Method or by the Ultracentrifugation Method, all in the Test Methods below. Accordingly, a surfactant phase of the multiphase composition of the present invention is considered "structured," if the surfactant phase has one or more of the following properties described below according to the Yield Stress Method, or the Zero Shear Viscosity Method or by the Ultracentrifugation Method. A surfactant phase is considered to be structured, if the phase has one or more of the following characteristics:

A. a Yield Stress of greater than about 0.1 Pascal (Pa), more preferably greater than about 0.5 Pa, even more preferably greater than about 1.0 Pa, still more preferably greater than about 2.0 Pa, still even more preferably greater than about 3 Pa, and even still even more preferably greater than about 5 Pa as measured by the Yield Stress and Zero Shear Viscosity Method described hereafter:

B. a Zero Shear Viscosity of at least about 500 Pascal-seconds (Pa-s), preferably at least about 1,000 Pa-s, more preferably at least about 1,500 Pa-s, even more preferably at least about 2,000 Pa-s; or C. a Structured Domain Volume Ratio as measured by the Ultracentrifugation Method described hereafter, of greater than about 40%, preferably at least about 45%, more preferably at least about 50%, more preferably at least about 55%, more preferably at least about 60%, more preferably at least about 65%, more preferably at least about 70%, more preferably at least about 75%, more preferably at least about 80%, even more preferably at least about 85%.

The term "visually distinct phase" as used herein, refers to a region of the multi-phase personal care composition having one average composition, as distinct from another region having a different average composition, wherein the regions are visible to the unaided naked eye. This would not preclude the distinct regions from comprising two similar phases where one phase could comprise pigments, dyes, particles, and various optional ingredients, hence a region of a different average composition. A phase generally occupies a space or spaces having dimensions larger than the colloidal or sub-colloidal components it comprises. A phase may also be constituted or re-constituted, collected, or separated into a bulk phase in order to observe its properties, e.g., by centrifugation, filtration or the like.

The multi-phase personal care composition of the present invention is typically extrudable or dispensible from a package. The multi-phase personal care compositions typically exhibit a viscosity of from about 1,500 centipoise (cP) to about 1,000,000 cP, as measured by the Viscosity Method as described in copending application Ser. No. 10/841,174 filed on May 7, 2004 titled "Mulit-phase Personal Care Compositions."

When evaluating a structured multi-phase personal care composition, by the methods described herein, preferably each individual phase is evaluated prior to combining, unless otherwise indicated in the individual methodology. However, if the phases are combined, each phase can be separated by centrifugation, ultracentrifugation, pipetting, filtering, washing, dilution, concentration, or combination thereof, and then the separate components or phases can be evaluated. Preferably, the separation means is chosen so that the resulting separated components being evaluated is not destroyed, but is representative of the component as it exists in the structured multi-phase personal care composition, i.e., its composition and distribution of components therein is not substantially altered by the separation means. Generally, multi-phase compositions comprise domains significantly larger than colloidal dimensions so that separation of the phases into the bulk is relatively easy to accomplish while retaining the colloidal or microscopic distribution of components therein. Prefebably, the compositions of the present invention are rinse-off formulations, by which is meant the product is applied topically to the skin or hair and then subsequently (i.e., within minutes) the skin or hair is rinsed with water, or otherwise wiped off using a substrate or other suitable removal means with deposition of a portion of the composition.

In a preferred embodiment of the present invention the structured multi-phase personal care composition comprises at least two visually distinct phases wherein a first phase is visually distinct from a second phase. Preferably, the visually distinct phases are packaged in physical contact with one another and are stable. Preferably, the visually distinct phases form a pattern.

The multi-phase personal care compositions of the present invention comprise at least two visually distinct phases, wherein the composition can have a first structured phase, a second phase, a third phase, a fourth phase and so on. The ratio of a first phase to a second phase is preferably from about 1:99 to about 99:1, preferably from about 90:10 to about 10:90, more preferably from about 80:20 to about 20:80, even more preferably from about 70:30 to about 30:70, still even more preferably from about 60:40 to about 40:60, even still even more preferably about 50:50.

The multi-phase personal care composition of the present invention can comprise a cleansing phase. The cleansing phase preferably comprises at least one branched anionic surfactant. Preferably, the structured surfactant component comprises a mixture of surfactants. The structured multiphase personal care composition typically comprises from about 1% to about 99%, by weight of the composition, of the cleansing phase.

The structured surfactant component preferably comprises a lathering surfactant or a mixture of lathering surfactants. The structured surfactant component preferably comprises at least one branched anionic surfactant. The structured surfactant component comprises surfactants suitable for application to the skin or hair. Suitable surfactants for use herein include any known or otherwise effective cleansing surfactant suitable for application to the skin, and which are otherwise compatible with the other essential ingredients in the structured multi-phase personal care composition including water. These surfactants include anionic, nonionic, cationic, zwitterionic, amphoteric surfactants, soap, or combinations thereof. Preferably, anionic surfactant comprises at least 40% of the structured surfactant component, more preferably from about 45% to about 95% of the structured surfactant component, even more preferably from about 50% to about 90%, still more preferably from about 55% to about 85%, and even still most preferably at least about 60% of the structured surfactant component comprises anionic surfactant.

The multi-phase personal care composition preferably comprises a structured surfactant component at concentrations ranging from about 2% to about 23.5%, more preferably from about 3% to about 21%, even more preferably from about 4% to about 20.4%, still more preferably from about 5% to about 20%, still even more preferably from about 13% to about 18.5%, and even still even more preferably from about 14% to about 18%, by weight of the cleansing phase.

The cleansing phase comprising the structured surfactant component is preferably a structured domain comprising surfactants. The structured domain enables the incorporation of high levels of benefit components in a separate phase that are not emulsified in the composition. In a preferred embodiment the structured domain is an opaque structured domain. The opaque structured domain is preferably a lamellar phase. The lamellar phase produces a lamellar gel network. The lamellar phase can provide resistance to shear, adequate yield to suspend particles and droplets and at the same time provides long term stability, since it is thermodynamically stable. The lamellar phase tends to have a higher viscosity thus minimizing the need for viscosity modifiers.

The cleansing phase typically provides a Total Lather Volume of at least about 600 ml, preferably greater than about 800 ml, more preferably greater than about 1000 ml, even more preferably greater than about 1200 ml, and still more preferably greater than about 1500 ml, as measured by the Lather Volume Test described hereafter. The cleansing phase preferably has a Flash Lather Volume of at least about 300 ml, preferably greater than about 400 ml, even more preferably greater than about 500 ml, as measured by the Lather Volume Test described hereafter.

Suitable surfactants are described in McCutcheon's, Detergents and Emulsifiers, North American edition (1986), published by allured Publishing Corporation; and McCutcheon's, Functional Materials, North American Edition (1992); and in U.S. Pat. No. 3,929,678 issued to Laughlin, et al on Dec. 30, 1975.

Suitable surfactants are described in McCutcheon's, Detergents and Emulsifiers, North American edition (1986), published by allured Publishing Corporation; and McCutcheon's, Functional Materials, North American Edition (1992); and in U.S. Pat. No. 3,929,678 issued to Laughlin, et al on Dec. 30, 1975.

Preferred linear anionic surfactants for use in the structured surfactant phase of the multiphase, personal care composition include ammonium lauryl sulfate, ammonium laureth sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, potassium lauryl sulfate, and combinations thereof.

Amphoteric surfactants are suitable for use in the multiphase composition of the present invention. The amphoteric surfactants include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, and N-alkyltaurines. Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the multiphase, personal care composition include betaines, including cocoamidopropyl betaine.

Non-limiting examples of preferred nonionic surfactants for use herein are those selected form the group consisting of glucose amides, alkyl polyglucosides, sucrose cocoate, sucrose laurate, alkanolamides, ethoxylated alcohols and mixtures thereof. In a preferred embodiment the nonionic surfactant is selected from the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

Preferably the nonionic surfactant has an HLB from about 1.0 to about 15.0, preferably from about 3.4 to about 15.0, more preferably from about 3.4 to about 9.5, even more preferably from about 3.4 to about 5.0. The multi-phase personal care composition preferably comprises a nonionic surfactant at concentrations ranging from about 0.01% to about 50%, more preferably from about 0.10% to about 10%, and even more preferably from about 0.5% to about 5.0%, by weight of the surfactant component.

Mixtures of anionic surfactants can be used in some embodiments, including mixtures of linear and branched surfactants, and anionic surfactants combined with nonionic, amphoteric, and/or zwitterionic surfactants.

An electrolyte, if used, can be added per se to the multiphase personal care composition or it can be formed in situ via the counterions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium chloride, ammonium chloride, sodium or ammonium sulfate. The electrolyte is preferably added to the structured surfactant phase of the composition in the amount of from about 0.1% to about 15% by weight, preferably from about 1% to about 6% by weight, more preferably from about 3% to about 6%, by weight of the structured surfactant composition.

In one embodiment of the present invention, the multiphase, personal care composition comprises a structured surfactant phase comprising a mixture of at least one nonionic surfactant, and an electrolyte. In another embodiment, the surfactant phase can comprise a mixture of surfactants, water, at least one anionic surfactant, an electrolyte, and at least one alkanolamide.

At least one anionic surfactant comprising anionic surfactant molecules of the present invention is preferably branched. A surfactant molecule is branched when the hydrocarbon tail of the surfactant molecule comprises at least one ternary or quaternary carbon atom, such that a methyl, ethyl, propyl, butyl, pentyl or hexyl side chain extends from the hydrocarbon backbone. The hydrocarbon backbone is described by the longest hydrocarbon length in the hydrocarbon tail. A side chain in the branched hydrocarbon of a surfactant molecule can be described by its position on the backbone, counting from the first carbon attached to a hydrophilic atom, enumerated as carbon number 1, the adjacent carbon on the backbone being carbon number 2, and so on. Side chains are also described by their length, a single carbon side chain denoted methyl; a 2-carbon length denoted ethyl, and so on. Side chains that have their own branching are denoted by conventional nomenclature techniques, e.g., isopropyl, but are less common. Anionic surfactant molecules which do not have branching are linear anionic surfactant molecules, and surfactants comprising a preponderance of linear anioinic surfactant molecules as indicated hereafter are linear anionic surfactants. Most anionic surfactants derived from common natural sources such as coconut and palm, are linear anionic surfactants, such as ammonium lauryl sulfate, sodium lauryl ether sulfate. Linear anionic surfactants can also be derived from other sources including synthetic.

Because an anionic surfactant typically comprises a mixture of different types of surfactant molecules, anionic surfactants can be called linear or branched depending on the relative amounts of individual surfactant molecules of different types that comprise the anionic surfactant. For example, sodium tridecyl sulfate and sodium trideceth sulfate can be called branched surfactants because they typically comprise nearly all (>95%) branched surfactant molecules. For the purposes of the present invention, an anionic surfactant is considered branched surfactant when at least 10% of its hydrocarbon chains are branched molecules.

Branched anionic surfactants comprise surfactant molecules having different kinds of branching. Some branched anionic surfactants, such as tridecanol based sulfates such as sodium trideceth sulfate, comprise a high level of branching, with over 80% of surfactant molecules comprising at least 2 branches and having an average of about 2.7 branches per molecule in some sodium trideceth sulfates. Other branched anionic surfactants, such as $C_{12-13}$ alkyl sulfate derived from Safol™ 23 alcohol (Sasol, Inc, Houston, Tex., USA) comprise a mixture of about 50-55% linear anionic surfactant molecules, with about 15-30% branched surfactant molecules. For the purposes of the present invention, anionic surfactants comprising more than 10% branched surfactant molecules, but having an average of less than 2.0 branches per molecule, are considered monomethyl branched anionic surfactants.

Branching information for many surfactants is typically known or obtainable from suppliers of branched alcohol feedstocks. For example, Sasol publishes the following information related to Safol™ 23 primary alcohol:

| Linear Alcohol Isomers | 50% |
|---|---|
| Mono-Methyl Alcohol Isomers | 30% |
| Other Primary Alcohol Isomers | <20% |
| Total | 100% |

Safol™ 23 alcohol can be sulfated, for example in an $SO_3$/air stream falling film reactor followed by rapid neutralization with sodium hydroxide to produce sodium $C_{12-13}$ alkyl sulfate, a process known in the art. Since the sulfation process involves no rearrangement of the hydrocarbon backbone, the backbone of the $C_{12-13}$ alkyl sulfate has the same structure as the Safol™ 23 alcohol, and is a branched anionic surfactant, and is also a monomethyl branched anionic surfactant. Other suppliers of alcohols provide similar information on their primary alcohols, e.g., Shell Chemical for the Neodol™ primary alcohols. In the absence of published analytical information by established methods from material suppliers on branching of a surfactant or its feedstock alcohol, analytical techniques known to those skilled in the art can be used to determine branching. For example, when the structure of the hydrocarbon tail is not very complex (i.e., less than about a dozen major components), a gas chromatography—mass spectrometry (GC-MS) technique can be used, involving oxidation of the alcohol in acetone (cosolvent) by a 3.3 M $H_2CRO_4$ Jones Reagent to a fatty acid followed by oxazoline derivatization using 2-amino, 2-methyl, 1-propanol at 200 C for 2 hours, dilution with $CHCl_3$ and subsequent washing with distilled water, drying with sodium sulfate prior to injection into a split injection (280 C) or on-column injection. A typical GC program is 80-320 C at 5 C/min rate on a 30 m×0.25 mm DB-1 (0.25 uM film) column, and can give specific information on branching location for a majority of a hydrocarbon tail of an anionic surfactant. When co-elution of species and/or elution of unknown components occurs, GC-MS is able to obtain the amount of branched components, which is taken as 100% minus the sum of n-C12 and n-C13 eluted. Typically, n-$C_{11}$, n-$C_{12}$ and n-$C_{13}$ elution times are known for a column and/or can be obtained by simple running of standards which are available. By convention for our invention, inventors sum all oxazoline peaks in the GC window between n-$C_{11}$ and n-$C_{12}$, said peaks are the branched $C_{12}$ peaks; sum all oxazoline peaks in the GC window between n-$C_{12}$ and n-$C_{13}$, said peaks are the branched $C_{13}$ peaks; dividing the peak areas obtained by the total area obtained, including linear $C_{12}$ and linear $C_{13}$, to obtain the fractional amount of each component. By our convention, the sum of the peak fractions in the branched $C_{12}$ and branched $C_{13}$ windows, added together, is the fraction of branched molecules, which can be expressed as a percentage. The integrated area under each GC peak is the peak information used in the calculations. If necessary, the surfactant can even be obtained by extraction from a composition first, e.g. by filtration such as crossflow filtration. From the GC data, the number of branch points per hydrocarbon chain is summed, multiplying number of branches per molecule by mole fraction for each species identified to obtain an average degree of branching per molecule for the surfactant. For example, 50% of molecules having 1 branch point with 50% linear molecules is an average degree of branching of 0.5. For highly branched molecules (>1.25 average degree of branching), such as sodium trideceth sulfate, determining degree of branching from the GC spectra can be difficult and require specialized equipment, so instead is determined from conventional NMR techniques, using the ratio of ternary to secondary carbon-carbon bonds in the hydrocarbon tail to determine average degree of branching.

Branched anionic surfactants include but are not limited to the following surfactants: sodium trideceth sulfate, sodium tridecyl sulfate, sodium $C_{12-13}$ alkyl sulfate, sodium $C_{12-15}$ alkyl sulfate, sodium $C_{11-15}$ alkyl sulfate, sodium $C_{12-18}$ alkyl sulfate, sodium $C_{10-16}$ alkyl sulfate, sodium $C_{12-13}$ pareth sulfate, sodium $C_{12-13}$ pareth-n sulfate, and sodium $C_{12-14}$ pareth-n sulfate. Other salts of all the aforementioned surfactants are useful, such as TEA, DEA, ammonia, potassium salts. Useful alkoxylates include the ethylene oxide, propylene oxide and EO/PO mixed alkoxylates. Phosphates, carboxylates and sulfonates prepared from branched alcohols are also useful anionic branched surfactants. Branched surfactants can be derived from synthetic alcohols such as the primary alcohols from the liquid hydrocarbons produced by Fischer-Tropsch condensed syngas, for example Safol™ 23 Alcohol available from Sasol North America, Houston, Tex.; from synthetic alcohols such as Neodol™ 23 Alcohol available from Shell Chemicals, USA; from synthetically made alcohols such as those described in U.S. Pat. No. 6,335,312 issued to Coffindaffer, et al on Jan. 1, 2002. Preferred alcohols are Safol™ 23 and Neodol™ 23. Preferred alkoxylated alcohols are Safol™ 23-3 and Neodol™ 23-3. Sulfates can be prepared by conventional processes to high purity from a sulfur based $SO_3$ air stream process, chlorosulfonic acid process, sulfuric acid process, or Oleum process. Preparation via $SO_3$ air stream in a falling film reactor is a preferred sulfation process.

Monomethyl branched anionic surfactants include but are not limited to the branched anionic sulfates derived from Safol™ 23-n and Neodol™ 23-n as previously described, where n is an integer between 1 and about 20. Fractional alkloxylation is also useful, for example by stoichiometrically adding only about 0.3 moles EO, or 1.5 moles EO, or 2.2 moles EO, based on the moles of alcohol present, since the molecular combinations that result are in fact always distributions of alkoxylates so that representation of n as an integer is merely an average representation. Preferred monomethyl branched anionic surfactants include a $C_{12-13}$ alkyl sulfate derived from the sulfation of Safol™ 23, which has about 28% branched anionic surfactant molecules; and a C12-13 pareth sulfate derived from Neodol™ 23-3, which has about 10-18% branched anionic surfactant molecules.

When the anionic surfactant is a branched anionic primary sulfate, it may contain some of the following branched anionic surfactant molecules: 4-methyl undecyl sulfate, 5-methyl undecyl sulfate, 7-methyl undecyl sulfate, 8-methyl undecyl sulfate, 7-methyl dodecyl sulfate, 8-methyl-dodecyl sulfate, 9-methyl dodecyl sulfate, 4,5-dimethyl decyl sulfate, 6,9-dimethyl decyl sulfate, 6,9-dimethyl undecyl sulfate, 5-methyl-8-ethyl undecyl sulfate, 9-methyl undecyl sulfate, 5,6,8-trimethyl decyl sulfate, 2-methyl dodecyl sulfate, and 2-methyl undecyl sulfate. When the anionic surfactant is a primary alkoxylated sulfate, these same molecules may be present as the n=0 unreacted alcohol sulfates, in addition to the typical alkoxylated adducts that result from alkoxylation (e.g., Neodol™ 23-3 mol EO retains typically 16% unreacted Neodol™ 23 with 57% of molecules having 1 to 5 EO molecules reacted, according to Shell Chemicals technical literature, "Typical Distributions of NEODOL Ethoxylate Adducts").

The density modifier of the present invention can be comprised in the surfactant component. These density modifiers are preferably low density microspheres. When the structured surfactant component comprises low density particles such that all parts of the structured composition are exposed to buoyant forces by the dispersed low density phase and the low density particles, creaming and phase separation are mitigated and the composition can be stabilized even under harsh conditions such as high temperature shipping and storage conditions. Preferably, a large number of low density particles are added so that all parts of the structured surfactant composition are exposed to buoyant forces. For example, in a composition comprising, by volume, 70% structured surfactant and 30% dispersed lipid wherein the lipid is dispersed to a size of 50 micron diameter, the yield stress to stabilize a single particle under a 10 g acceleration (e.g., during shipping) can be calculated to be about 0.21 Pa, assuming monodispersed lipid droplets in a cubic array with a homogenous stress distribution over the cube faces. When the volume fraction of lipid is increased to 50% of the same composition, the required yield stress can be calculated to be 0.30 Pa, due to the more concentrated stress per individual particle. Thus, one would expect that increasing the number of low density dispersed phase droplets would destabilize the composition, which has been the experience of the inventors. Conventionally, one would expect that introducing other low density, dispersed domains of any kind would also lead to instability by the same mechanism—increased stress concentration required to stabilize each individual dispersed domain.

However, introducing particular buoyant particles to compositions comprising a dispersed hydrophobic phase has a tendency to exert a stabilizing, not a destabilizing, effect on the composition. The stabilizing effect may be related to the density difference between the added buoyant particles and the dispersed hydrophobic phase. For example, when the added buoyant particles have a density of about 25 kg/m³ (i.e., 0.025 gm/cm³), and the dispersed hydrophobic phase is petrolatum which has a density of about 0.88 gm/cm³, the buoyant particles are 0.855 gm/cm³ lower in density than the hydrophobic phase, leading to essentially 'superbuoyant regions' of composition comprising a buoyant particle and structured surfactant surrounding the particle, which reduces the gravitational force on the structured surfactant in the region adjacent to the particle. Given a sufficient number of buoyant particles, the net contribution of the buoyant particles can be to increase stability of compositions comprising both the buoyant particles and a dispersed hydrophobic phase in a structured surfactant composition. For example, when 0.30 weight % of buoyant particles having an average density of 25 kg/m³ is added to a composition, the effective volume of the composition increases by about 10%. If the particles are about 50 micron diameter, about $1.5*10^8$ buoyant particles are added per 100 grams of composition, resulting in a substantial number of superbouyant particle domains.

Preferably, the buoyant particles have a density of less than 0.85 gm/cm³, more preferably less than about 0.5 gm/cm³, still more preferably less than about 0.1 gm/cm³, even more preferably less than about 0.05 gm/cm³.

When the amount of a low density benefit component is increased in the composition; the need for density modifiers is also increased. Specifically, the need to add density modifier to the surfactant component is increased when (1) the benefit component is a hydrophobic material (petrolatum, e.g., having a lower density than the cleansing phase); (2) the amount of 'petrolatum' is higher than 20%, even 30%, even about 40% or more of the composition.

To further improve stability under stress conditions such as high temperature and vibration, it is preferable to adjust the densities of the separate components, such that they are substantially equal. To achieve this, low density microspheres can be added to the surfactant component of the mild, structured, multiphase cleansing composition. The low density microspheres employed to reduce the overall density of the surfactant component are particles having a density lower than 0.7 g/cm$^3$, preferably less than 0.2 g/cm$^3$, more preferably less than 0.1 g/cm$^3$, most preferably less than 0.05 g/cm$^3$. The low density microspheres generally have a diameter less than 200 μm, preferably less than 100 μm, most preferably less than 40 μm. Preferably, the density difference between the first density of the surfactant component when the surfactant component comprises the low density particles and the second density of the benefit component is less than 0.15 g/cm$^3$, more preferably, the density difference is less than 0.10 g/cm$^3$, even more preferably, the density difference is less than 0.08 g/cm$^3$, still more preferably, the density difference is less than 0.06 g/cm$^3$, still even more preferably, the density difference is less than 0.05 g/cm$^3$, most preferably, the density difference is less than 0.02 g/cm$^3$.

When the benefit component comprising hydrophobic materials such as petrolatum, mineral oil, waxes, hydrophobic polymers, fatty esters, fatty ethers, and/or triglycerides which have a density is blended with a structured surfactant component, the resulting blended composition has a density indicative of the mixture. For example, a multiphase personal cleansing composition comprises 15% petrolatum having a density of 0.88 g/cm$^3$ mixed with a 85% of a surfactant component having a density of 1.0 g/cm$^3$ has a density of about 0.982 g/cm$^3$, but if the surfactant component utilizes low density particles to reduce its density to 0.93 g/cm$^3$, the resultingresulting multiphase personal cleansing composition has a density of about 0.923 g/cm$^3$.

Preferably, the structured surfactant phase comprises low density particles so that the blended composition has a low density. When the structured surfactant phase comprises low density particles, the density of the composition (i.e., hydrophobic phase combined with surfactant phase) is preferably less than about 0.97 g/cm$^3$, more preferably less than about 0.96 g/cm$^3$, even more preferably less than about 0.95 g/cm$^3$, still more preferably less than about 0.94 g/cm$^3$, still even more preferably less than about 0.92 g/cm$^3$, most preferably less than about 0.90 g/cm$^3$.

The microspheres are produced from any appropriate inorganic or organic material, compatible with a use on the skin, that is, nonirritating and nontoxic. Preferably, the microspheres don't negatively impact the product lather performance.

Expanded microspheres made of thermoplastic material are known, and may be obtained, for example, according to the processes described in Patents and Patent Applications EP-56219, EP-348372, EP-486080, EP-320473, EP-112807 and U.S. Pat. No. 3,615,972.

These microspheres may be produced from any nontoxic and non-irritant thermoplastic materials. These microspheres can be in the dry or hydrated state. Among hollow microspheres which can be used, special mention may be made of those marketed under the brand name EXPANCEL® (thermoplastic expandable microspheres) by the Akzo Nobel Company, especially those of DE (dry state) or WE (hydrated state) grade. Representative microspheres derived from an inorganic material, include, for instance, "QCEL® Hollow Microspheres" and "EXTENDOSPHERES"™ Ceramic Hollow Spheres", both available from the PQ Corporation. Examples are: Qcel® 300; Qcel® 6019; Qcel® 6042S.

Benefit Phase

The multiphase personal care compositions of the present invention can comprise a benefit phase. The benefit phase in the present invention is preferably anhydrous and can be substantially free of water. The benefit phase can comprise less than about 5% water, preferable less than 3% water or most preferably less than 1% water. The benefit phase can be substantially free of surfactant. The benefit phase can comprise less than about 5% of surfactant, more preferably less than about 3% of surfactant and most preferably less than about 1% surfactant.

The benefit phase typically comprises hydrophobic moisturizing materials. The benefit phase can be comprised of the components selected from the group consisting of petrolatum, lanolin, hydrocarbon oils such as mineral oil, natural and synthetic waxes such as micro-crystalline waxes, paraffins, ozokerite, lanolin wax, lanolin alcohols, lanolin fatty acids, polyethylene, polybutene, polydecene and perhydrosqualene, volatile or non-volatile organosiloxanes and their derivatives such as dimethicones, cyclomethicones, alkyl siloxanes, polymethylsiloxanes and methylphenylpolysiloxanes, lanolin oil, esters such as isopropyl lanolate, acetylated lanolin, acetylated lanolin alcohols, lanolin alcohol linoleate, lanolin alcohol riconoleate natural and synthetic triglycerides such as castor oil, soy bean oil, sunflower seed oil, maleated soy bean oil, safflower oil, cotton seed oil, corn oil, walnut oil, peanut oil, olive oil, cod liver oil, almond oil, avocado oil, palm oil and sesame oil, and combinations thereof.

The benefit phase may comprise from about 1% to about 100%, preferably at least about 15%, preferably at least about 17.5%, preferably at least about 20%, preferably at least about 24%, preferably at least about 30%, by weight of the benefit phase, of a hydrophobic moisturizing material. Hydrophobic moisturizing materials suitable for use in the present invention preferably have a Vaughan Solubility Parameter of from about 5 (cal/cm$^3$)$^{1/2}$ to about 15 (cal/cm$^3$)$^{1/2}$, as defined by Vaughan in *Cosmetics and Toiletries*, Vol. 103. Non-limiting examples of hydrophobic moisturizing materials having VSP values ranging from about 5 to about 15 include the following: Cyclomethicone 5.92, Squalene 6.03, Petrolatum 7.33, Isopropyl Palmitate 7.78, Isopropyl Myristate 8.02, Castor Oil 8.90, Cholesterol 9.55, as reported in *Solubility, Effects in Product, Package, Penetration and Preservation*, C. D. Vaughan, Cosmetics and Toiletries, Vol. 103, October 1988.

The hydrophobic materials are preferably selected among those having defined rheological properties as described hereinafter, including selected Consistency value (K) and Shear Index (n). These preferred Theological properties are especially useful in providing the personal care compositions with lubrication of the skin surface for shaving and for improved deposition of hydrophobic moisturizing materials. The benefit phase has a Consistency Value (K) from about 20 to about 2,000 Pa-s, preferably from about 25 to about 500 Pa-s, more preferably from about 30 to about 450 Pa-s, still more preferably from about 30 to about 400 Pa-s and even still more preferably from about 30 to about 350 Pa-s. The benefit phase has a Shear Index from about 0.025 to about 0.99.

Examples of suitable benefit phases and description of measuring the values of Consistency (K) and Shear Index (n) are described in U.S. patent application Ser. No. 10/665,670, Publication No. 2004/0057920 A1 entitled Striped liquid personal cleansing compositions containing a cleansing phase and a separate benefit phase" filed by Fact, et al. on Sep. 18, 2003, published on Apr. 4, 2004, U.S. patent application Ser. No. 10/699,469 Publication No. 2004/0092415 A1 entitled "Striped liquid personal cleansing compositions containing a cleansing phase and a separate benefit phase with improved stability" filed by Fact, et al. on Oct. 31, 2003, published on May 13, 2004 and U.S. patent application Ser. No. 10/837,214 Publication No. 2004/0219119 A1 entitled "Visually distinctive multiple liquid phase compositions" filed by Weir, et al. on Apr. 30, 2004, published on Nov. 18, 2004.

The density modifiers of the present invention can be comprised in the benefit component. Just as low density microspheres can be added to the structured surfactant component of the present invention to improve stability, high density materials can be added to the benefit component to increase its density having the same impact on stability. The high density particles employed to increase the overall density of the benefit component are particles having a density greater than 1.1 g/cm$^3$, preferably greater than 1.5 g/cm$^3$, more preferably greater than 2.0 g/cm$^3$, most preferably greater than 2.5 g/cm$^3$. The high density particles generally have a diameter less than 200 µm, preferably less than 100 µm, most preferably less than 40 µm. Preferably, the high density particles are selected from water-insoluble inorganic materials, metals, metal oxides, metal alloys and mixture thereof. Non-limiting examples include calcium carbonate, silica, clays, mica, talc, iron, zinc, copper, lead, titanium dioxide, zinc oxide, and the like.

Structured Aqueous Phase

The multi-phase personal care compositions of the present invention can comprise a structured aqueous phase that comprises a water structurant and water. The structured aqueous phase can be hydrophilic and in a preferred embodiment the structured aqueous phase is a hydrophilic, non-lathering, gelled water phase. In addition, the structured aqueous phase typically comprises less than about 5%, preferably less than about 3%, and more preferably less than about 1%, by weight of the structured aqueous phase, of a surfactant. In one embodiment of the present invention, the structured aqueous phase is free of lathering surfactant in the formulation. A preferred structured aqueous phase is a non-lathering structured aqueous phase as described in published U.S. Patent Application No. 2005/0143269A1 entitled "Multi-phase Personal Cleansing Compositions Containing A Lathering Cleansing Phase And A Non-Lathering Structured Aqueous Phase."

The structured aqueous phase of the present invention can comprise from about 30% to about 99%, by weight of the structured aqueous phase, of water. The structured aqueous phase generally comprises more than about 50%, preferably more than about 60%, even more preferably more than about 70%, and still more preferably more than about 80%, by weight of the structured aqueous phase, of water.

The structured aqueous phase will typically have a pH of from about 5 to about 9.5, more preferably about 7. A water structurant for the structured aqueous phase can have a net cationic charge, net anionic charge, or neutral charge. The structured aqueous phase of the present compositions can further comprise optional ingredients such as, pigments, pH regulators (e.g. triethanolamine), and preservatives.

The structured aqueous phase can comprise from about 0.1% to about 30%, preferably from about 0.5% to about 20%, more preferably from about 0.5% to about 10%, and even more preferably from about 0.5% to about 5%, by weight of the structured aqueous phase, of a water structurant.

The water structurant is typically selected from the group consisting of inorganic water structurants, charged polymeric water structurants, water soluble polymeric structurants, associative water structurants, and mixtures thereof. Non-limiting examples of inorganic water structurants include silicas, polymeric gellants such as polyacrylates, polyacrylamides, starches, modified starches, crosslinked polymeric gellants, copolymers, and mixtures thereof. Non-limiting examples of charged polymeric water structurants for use in the multi-phase personal care composition include Acrylates/Vinyl Isodecanoate Crosspolymer (Stabylen 30 from 3V), Acrylates/C10-30 Alkyl Acrylate Crosspolymer (Pemulen TR1 and TR2), Carbomers, Ammonium Acryloyldimethyltaurate/VP Copolymer (Aristoflex AVC from Clariant), Ammonium Acryloyldimethyltaurate/Beheneth-25 Methacrylate Crosspolymer (Aristoflex HMB from Clariant), Acrylates/Ceteth-20 Itaconate Copolymer (Structure 3001 from National Starch), Polyacrylamide (Sepigel 305 from SEPPIC), and mixtures thereof. Non-limiting examples of water soluble polymeric structurants for use in the multi-phase personal care composition include cellulose gums and gel, and starches. Non-limiting examples of associative water structurants for use in the multi-phase personal care composition include xanthum gum, gellum gum, pectins, alginates such as propylene glycol alginate, and mixtures thereof.

Additional Ingredients

The phases of the multi-phase personal care composition, preferably the cleansing phase, can further comprise a polymeric phase structurant. The compositions of the present invention typically can comprise from about 0.05% to about 10%, preferably from about 0.1% to about 4%, of a polymeric phase structurant. Non-limiting examples of polymeric phase structurant include but are not limited to the following examples: naturally derived polymers, synthetic polymers, crosslinked polymers, block copolymers, copolymers, hydrophilic polymers, nonionic polymers, anionic polymers, hydrophobic polymers, hydrophobically modified polymers, associative polymers, and oligomers.

Preferably the polymeric phase structurant can be crosslinked and further comprise a crosslinking. These polymeric phase structurant useful in the present invention are more fully described in U.S. Pat. No. 5,087,445, to Haffey et al., issued Feb. 11, 1992; U.S. Pat. No. 4,509,949, to Huang et al., issued Apr. 5, 1985, U.S. Pat. No. 2,798,053, to Brown, issued Jul. 2, 1957. See also, CTFA International Cosmetic Ingredient Dictionary, fourth edition, 1991, pp. 12 and 80.

The phase of the present compositions, preferably the cleansing phase, optionally can further comprise a liquid crystalline phase inducing structurant, which when present is at concentrations ranging from about 0.3% to about 15%, by weight of the phase, more preferably at from about 0.5% to about 5% by weight of the phase. Suitable liquid crystalline phase inducing structurants include fatty acids (e.g. lauric acid, oleic acid, isostearic acid, linoleic acid) ester derivatives of fatty acids (e.g. propylene glycol isostearate, propylene glycol oleate, glyceryl isostearate) fatty alcohols, trihydroxystearin (available from Rheox, Inc. under the trade name THIXCIN® R). Preferably, the liquid crystalline phase inducing structurant is selected from lauric acid, trihydroxystearin, lauryl pyrrolidone, and tridecanol.

The structured multi-phase personal care compositions of the present invention can additionally comprise an organic cationic deposition polymer in the one or more phases as a deposition aid for the benefit agents described herein. Suitable cationic deposition polymers for use in the structured multi-phase personal care compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the structured multi-phase personal care composition. Suitable cationic deposition polymers that would be useful in the compositions of the present invention are disclosed in the co-pending and commonly assigned U.S. Patent Application No. 60/628,036 filed on Nov. 15, 2003 by Wagner, et al titled "Depositable Solids."

One or more of the phases of the multiphase personal care composition can comprise a variety of additional optional ingredients such as shiny particles, particles or beads, exfoliating beads. The multiphase personal care composition may compriseg a particle selected from the group consisting of natural, synthetic, semi-synthetic, hybrid, and combinations thereof. The exfoliant particle is preferably present at a level of less than about 10%, by weight of the composition, more about 5%, by weight of the composition, more preferably about 3% by weight of the composition, more preferably about 2% by weight of the composition, and more preferably about 1% by weight of the composition A water insoluble particle of various shapes and densities is useful. In a preferred embodiment, the particle tends to have a spherical, an oval, an irregular, or any other shape in which the ratio of the largest dimension to the smallest dimension (defined as the Aspect Ratio) is less than about 10, preferably less than about 8, and still more preferably the Aspect Ratio of the particle is less than about 5. Preferably, the particle will also have physical properties which are not significantly affected by typical processing of the composition.

The structured multi-phase personal care composition of the present invention can comprise an exfoliant particle. A preferred particle is selected from the group consisting of polyethylene, microcrystalline wax, jojoba esters, amourphors silica, talc, tracalcium orthophosphate, or blends thereof, and the like in at least one phase of the multi-phase personal care composition. The exfoliant particle is preferably present at a level of less than about 10%, by weight of the composition.

The structured multi-phase personal care compositions of the present invention can comprise a shiny particle in at least one phase of the multi-phase personal care composition. Non-limiting examples of shiny particles include the following: interference pigment, multi-layered pigment, metallic particle, solid and liquid crystals, and combinations thereof. An interference pigment is a pigment with pearl gloss prepared by coating the surface of a particle substrate material with a thin film. The particle substrate material is generally platelet in shape. The thin film is a transparent or semitransparent material having a high refractive index. The high refractive index material shows a pearl gloss resulting from mutual interfering action between reflection and incident light from the platelet substrate/coating layer interface and reflection of incident light from the surface of the coating layer. When pigment is applied and rinsed as described in the Pigment Deposition Tape Strip Method as described in copending application Ser. No. 60/469,075, filed on May 8, 2003, the deposited pigment on the skin is preferably at least 0.5 μg/cm$^2$, more preferably at least 1 μg/cm$^2$, and even more preferably at least 5 μg/cm$^2$. Interference pigments that are suitable for use in the compositions of the present invention are those disclosed in U.S. Pat. No. 6,395,691 issued to Liang Sheng Tsaur on May 28, 2002, U.S. Pat. No. 6,645,511 issued to Aronson, et al., U.S. Pat. No. 6,759,376 issued to Zhang, et al on Jul. 6, 2004, U.S. Pat. No. 6,780,826 issued on Aug. 24, 2004, U.S. Patent Application No. 2003/0054019 filed on May 21, 2002, published on Mar. 21, 2003 to Aronson, et al, as well as those pending and commonly assigned under U.S. Patent Application No. 60/469,570 filed on May 9, 2003 by Clapp, et al titled "Personal Care Compositions That Deposit Shiny Particles," and U.S. Patent Application No. 60/515,029 filed on Oct. 28, 2003, 2003 by Clapp, et al titled "Methods for Using Personal Care Compositions Containing Shiny Particles."

A portion of the interference pigment surface can be coated with a hydrophobic material. Hydrophobically modified interference pigments that are suitable for use in the compositions of the present invention are those disclosed in pending and commonly assigned under U.S. patent application Ser. No. 10/841,173 filed on May 7, 2004 by Clapp, et al titled "Personal Care Compositions Containing Hydrophobically Modified Interference Pigments."

Optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992.

Other non limiting examples of these optional ingredients include vitamins and derivatives thereof (e.g., ascorbic acid, vitamin E, tocopheryl acetate, and the like), sunscreens; thickening agents, preservatives for maintaining the anti microbial integrity of the cleansing compositions, anti-acne medicaments, antioxidants, skin soothing and healing agents such as aloe vera extract, allantoin and the like, chelators and sequestrants, skin lightening agents, and agents suitable for aesthetic purposes such as fragrances, essential oils, skin sensates, pigments, pearlescent agents and essential oils and fragrance.

The preferred pH range of the structured multi-phase personal care composition is from about 5 to about 8.

Method of Use

The mild, multiphase cleansing compositions of the present invention are preferably applied topically to the desired area of the skin or hair in an amount sufficient to provide effective delivery of the structured surfactant component, hydrophobic benefit material, and particles to the applied surface. The compositions can be applied directly to the skin or indirectly via the use of a cleansing puff, washcloth, sponge or other implement. The compositions are preferably diluted with water prior to, during, or after topical application, and then subsequently the skin or hair rinsed or wiped off, preferably rinsed off of the applied surface using water or a water-insoluble substrate in combination with water.

Method of Manufacture

The multi-phase personal care compositions of the present invention may be prepared by any known or otherwise effective technique, suitable for making and formulating the desired multi-phase product form. It is effective to combine toothpaste-tube filling technology with a spinning stage design. Additionally, the present invention can be prepared by the method and apparatus as disclosed in U.S. Pat. No. 6,213,166 issued to Thibiant, et al. on Apr. 10, 2001. The method and apparatus allows two or more compositions to be filled with a spiral configuration into a single container. The method requires that at least two nozzles be employed to fill the container. The container is placed on a static mixer and spun as the composition is introduced into the container.

Alternatively, it is effective to combine at least two phases by first placing the separate compositions in separate storage tanks having a pump and a hose attached. The phases are then pumped in predetermined amounts into a single combining section. Next, the phases are moved from the combining sections into the blending sections and the phases are mixed in the blending section such that the single resulting product exhibits a distinct pattern of the phases. The pattern is selected from the group consisting of striped, marbled, geometric, and mixtures thereof. The next step involves pumping the product that was mixed in the blending section via a hose into a single nozzle, then placing the nozzle into a container and filing the container with the resulting product. Specific non-limiting examples of such methods as they are applied to specific embodiments of the present invention are described in the following examples.

If the multi-phase personal care compositions are patterned, it can be desirable to be packaged as a personal care article. The personal care article would comprise these compositions in a transparent or translucent package such that the consumer can view the pattern through the package. Because of the viscosity of the subject compositions it may also be desirable to include instructions to the consumer to store the package upside down, on its cap to facilitate dispensing.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

Test Methods

Yield Stress and Zero Shear Viscosity Method: The Yield Stress and Zero Shear Viscosity of a phase of the present composition, can be measured either prior to combining in the composition, or after combining in the composition by separating the phase by suitable physical separation means, such as centrifugation, pipetting, cutting away mechanically, rinsing, filtering, or other separation means.

A controlled stress rheometer such as a TA Instruments AR2000 Rheometer is used to determine the Yield Stress and Zero Shear Viscosity. The determination is performed at 25° C. with the 4 cm diameter parallel plate measuring system and a 1 mm gap. The geometry has a shear stress factor of 79580 $m^{-3}$ to convert torque obtained to stress.

First a sample of the phase is obtained and placed in position on the rheometer base plate, the measurement geometry (upper plate) moving into position 1 mm above the base plate. Excess phase at the geometry edge is removed by scraping after locking the geometry. If the phase comprises particles discernible to the eye or by feel (beads, e.g.) which are larger than about 150 microns in number average diameter, the gap setting between the base plate and upper plate is increased to the smaller of 4 mm or 8-fold the diameter of the $95^{th}$ volume percentile particle diameter. If a phase has any particle larger than 5 mm in any dimension, the particles are removed prior to the measurement.

The determination is performed via the programmed application of a continuous shear stress ramp from 0.1 Pa to 1,000 Pa over a time interval of 5 minutes using a logarithmic progression, i.e., measurement points evenly spaced on a logarithmic scale. Thirty (30) measurement points per decade of stress increase are obtained. Stress, strain and viscosity are recorded. If the measurement result is incomplete, for example if material flows from the gap, results obtained are evaluated and incomplete data points excluded. The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log(stress) is graphed vs. log(strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form:

$$\text{Log(strain)} = m \ast \text{Log(stress)} + b \quad (1)$$

Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., $10^x$ for each x). The predicted strain is compared to the actual strain at each measurement point to obtain a % variation at each point, using Equation (2).

$$\% \text{ variation} = 100 \ast (\text{measured strain} - \text{predicted strain}) / \text{measured strain} \quad (2)$$

The Yield Stress is the first stress (Pa) at which % variation exceeds 10% and subsequent (higher) stresses result in even greater variation than 10% due to the onset of flow or deformation of the structure. The Zero Shear Viscosity is obtained by taking a first median value of viscosity in Pascal-seconds (Pa-sec) for viscosity data obtained between and including 0.1 Pa and the Yield Stress. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

Ultracentrifugation Method: The Ultracentrifugation Method is used to determine the percent of a structured domain or an opaque structured domain that is present in a structured multi-phase personal care composition that comprises a cleansing phase comprising a structured surfactant component. The method involves the separation of the composition by ultracentrifugation into separate but distinguishable layers. The structured multi-phase personal care composition of the present invention can have multiple distinguishable layers, for example a non-structured surfactant layer, a structured surfactant layer, and a benefit layer.

First, dispense about 4 grams of multi-phase personal care composition into Beckman Centrifuge Tube (11×60 mm). Next, place the centrifuge tubes in an Ultracentrifuge (Beckman Model L8-M or equivalent) and ultracentrifuge using the following conditions: 50,000 rpm, 18 hours, and 25° C.

After ultracentrifuging for 18 hours, determine the relative phase volume by measuring the height of each layer visually using an Electronic Digital Caliper (within 0.01 mm). First, the total height is measured as $H_a$ which includes all materials in the ultracentrifuge tube. Second, the height of the benefit layer is measured as $H_b$. Third, the structured surfactant layer is measured as $H_c$. The benefit layer is determined by its low moisture content (less than 10% water as measured by Karl Fischer Titration). It generally presents at the top of the centrifuge tube. The total surfactant layer height ($H_s$) can be calculated by this equation:

$$H_s = H_a - H_b$$

The structured surfactant layer components may comprise several layers or a single layer. Upon ultracentrifugation, there is generally an isotropic layer at the bottom or next to the bottom of the ultracentrifuge tube. This clear isotropic layer typically represents the non-structured micellar surfactant layer. The layers above the isotropic phase generally comprise higher surfactant concentration with higher ordered structures (such as liquid crystals). These structured layers are sometimes opaque to naked eyes, or translucent, or clear. There is generally a distinct phase boundary between the structured layer and the non-structured isotropic layer. The physical nature of the structured surfactant layers can be determined through microscopy under polarized light. The structured surfactant layers typically exhibit distinctive texture under polarized light. Another method for characterizing the structured surfactant layer is to use X-ray diffraction technique. Structured surfactant layer display multiple lines that are often associated primarily with the long spacings of the liquid crystal structure. There may be several structured layers present, so that $H_c$ is the sum of the individual structured layers. If a coacervate phase or any type of polymer-surfactant phase is present, it is considered a structured phase.

Finally, the structured domain volume ratio is calculated as follows:

$$\text{Structured Domain Volume Ratio} = H_c/H_s * 100\%$$

If there is no benefit phase present, use the total height as the surfactant layer height, $H_s = H_a$.

Lather Volume Test: Lather volume of a cleansing phase, a structured surfactant component or a structured domain of a structured multi-phase personal care composition, is measured using a graduated cylinder and a rotating apparatus. A 1,000 ml graduated cylinder is used which is marked in 10 ml increments and has a height of 14.5 inches at the 1,000 ml mark from the inside of its base (for example, Pyrex No. 2982). Distilled water (100 grams at 25° C.) is added to the graduated cylinder. The cylinder is clamped in a rotating device, which clamps the cylinder with an axis of rotation that transects the center of the graduated cylinder. Inject 0.50 grams of a structured surfactant component or cleansing phase from a syringe (weigh to ensure proper dosing) into the graduated cylinder onto the side of the cylinder, above the water line, and cap the cylinder. When the sample is evaluated, use only 0.25 cc, keeping everything else the same. The cylinder is rotated for 20 complete revolutions at a rate of about 10 revolutions per 18 seconds, and stopped in a vertical position to complete the first rotation sequence. A timer is set to allow 15 seconds for lather generated to drain. After 15 seconds of such drainage, the first lather volume is measured to the nearest 10 ml mark by recording the lather height in ml up from the base (including any water that has drained to the bottom on top of which the lather is floating).

If the top surface of the lather is uneven, the lowest height at which it is possible to see halfway across the graduated cylinder is the first lather volume (ml). If the lather is so coarse that a single or only a few foam cells which comprise the lather ("bubbles") reach across the entire cylinder, the height at which at least 10 foam cells are required to fill the space is the first lather volume, also in ml up from the base. Foam cells larger than one inch in any dimension, no matter where they occur, are designated as unfilled air instead of lather. Foam that collects on the top of the graduated cylinder but does not drain is also incorporated in the measurement if the foam on the top is in its own continuous layer, by adding the ml of foam collected there using a ruler to measure thickness of the layer, to the ml of foam measured up from the base. The maximum lather height is 1,000 ml (even if the total lather height exceeds the 1,000 ml mark on the graduated cylinder). 30 seconds after the first rotation is completed, a second rotation sequence is commenced which is identical in speed and duration to the first rotation sequence. The second lather volume is recorded in the same manner as the first, after the same 15 seconds of drainage time. A third sequence is completed and the third lather volume is measured in the same manner, with the same pause between each for drainage and taking the measurement.

The lather results after each sequence are added together and the Total Lather Volume determined as the sum of the three measurements, in milliters ("ml"). The Flash Lather Volume is the result after the first rotation sequence only, in ml, i.e., the first lather volume. Compositions according to the present invention perform significantly better in this test than similar compositions in conventional emulsion form.

The Shear Index (n) and Consistency Value (K): The Shear Index (n) and Consistency Value (K) are known and accepted means for reporting the viscosity profile of materials having a viscosity that varies with applied shear rate using a Power Law model. The term "Consistency value" or "K" as used herein is a measure of viscosity and is used in combination with Shear Index, to define viscosity for materials whose viscosity is a function of shear rate. The measurements of Consistency value and Shear Index are made at 25° C. The units for "Consistency value" or "K" are Pascal seconds. The units for "Shear Index" are dimensionless.

Viscosity of a phase can be measured by applying a shear stress and measuring the shear rate using a rheometer, such as a TA Instruments AR2000 (TA Instruments, New Castle, Del., USA 19720). Viscosity is determined at different shear rates in the following manner. First, the benefit phase is obtained. If there exists more than one distinct (immiscible, e.g.) benefit phase in the composition, such as for example a silicone oil phase and a hydrocarbon phase, they are preferably prepared separately and/or separated from each other, and evaluated separately from each other, although certain benefit phases which are mixtures such as emulsions can be evaluated as mixtures, in addition to evaluating the individual benefit phases individually.

For measurement, a 40 mm diameter parallel plate geometry with a gap of 1 mm is used unless there are particles greater than 0.25 mm, in which case a gap of 2 mm is used. The rheometer uses standard parallel plate conventions to report shear rate at the edge as shear rate of the test; and converts torque to stress using the factor $2/(\pi R^3)$. Using a spatula, a sample comprising a small excess of the benefit phase is loaded onto the rheometer base plate which is at 25° C., the gap is obtained, and excess composition outside the top measurement geometry is removed, locking the top plate in position during the removal of excess sample. The sample is equilibrated to the base plate temperature for 2 minutes. A preshear step is performed comprising 15 seconds of shear at a shear rate of 50 inverse seconds (1/sec). As is known to one skilled in the art, the shear rate with a parallel plate geometry is expressed as the shear rate at the edge, which is also the maximum shear rate. After the preshear step, the measurement is performed, which comprises ramping the stress from 10 Pa to 1,000 Pa over a 2.0 minute interval at 25° C., while collecting 60 viscosity data points, in an evenly spaced linear progression. A shear rate of at least 500 1/seconds is obtained in the test, or the test is repeated with a fresh sample of the same component with a higher final stress value, maintaining the same rate of stress increase per time, until a shear rate of at least 500 1/sec is obtained during the measurement period. During the measurement, observe the sample to make certain the area under the top parallel plate is not evacuated of sample at any edge location during the measurement, or the measurement is repeated until a sample remains for the duration of the test. If after several trials a result cannot be obtained due to sample evacuation at the edge, the measurement is repeated leaving an excess reservoir of material at the edge (not scraping). If evacuation still cannot be avoided, a concentric cylinder geometry is used with a large excess of sample to avoid air pockets during loading. The results are fitted to the power law model by selecting only the data points between 25-500 1/sec shear rate, viscosity in Pa-s, shear rate in 1/sec, and using a least squares regression of the logarithm of viscosity vs. the logarithm of shear rate to obtain values of K and n according to the Power Law equation:

$$\mu = K(\gamma')^{(n-1)}$$

The value obtained for the log-log slope is (n−1) where n is the Shear Index and the value obtained for K is the Consistency Value, expressed in units of in Pa-s.

Density Method: The metal pycnometer is utilized for determination of density of the individual phases, the surfactant phase and the benefit phase compositions. Density is measured in the absence of confounding factors such as whipped air bubbles which are generally kept to a minimum in commercial processes. A metal pycnometer can be obtained from Fisher Scientific (USA). Following are the steps for measuring density of cleansing phase and benefit phase compositions, and the multiphase personal cleansing composition. All instrument parts and phases are measured at ambient temperature.

The first step is Cleaning: The metal pycnometer must be clean and dry before use. Disassemble the metal pycnometer completely and wash all parts well with water. Follow the water rinse with an alcohol rinse. Expel the alcohol with a stream of dry, clean air.

The second step is to obtain the weight of the empty pycnometer, and get pycnometer volume: Fill the clean, dry pycnometer with distilled water at 25 C. Place the lid on body of pycnometer and screw the cap firmly in place. Dry the outside of pycnometer well with a tissue and weigh to 0.001 g. Remove the water, clean and dry the pycnometer according to the directions shown above. Assemble and weigh the dry, empty pycnometer to 0.001 g to obtain the weight of empty pycnometer. Calculate the Water Weight in grams, which is numerically the pycnometer volume in $cm^3$, using the assumption that the density of water is 1.00 $g/cm^3$.

Water Weight=Weight of pycnometer filled with water−Weight of Empty Pycnometer

The third step is the measurement of phase weight: Obtain a cleansing phase. The cleansing phase is preferably obtained prior to combining with a benefit phase, or it can be separated from a multiphase composition by physical means such as centrifugation, pipetting, etc. The phase can contain a density modifier. Clean and dry the pycnometer according to the directions shown above. Pour or otherwise fill the phase into the pycnometer without introducing air, adding an excess of the phase so that it extends slightly above the top of the pycnometer. Screw the cap firmly onto the body of the pycnometer: excess is forced through the hole in the lid of the pycnometer. Wipe away the excess. Weigh the filled pycnometer to 0.001 g to obtain the Weight of Filled Pycnometer. Calculate the Phase Weight according to the following equation.

Phase Weight=Weight of Filled Pycnometer−Weight of Empty Pycnometer.

The fourth step is tp calculate the Density of the phase according to the following equation:

Density of Phase=Sample Weight/Water Weight(express in $g/cm^3$).

The fifth step is repeat the procedure to obtain the Density of a benefit phase, using a benefit phase composition obtained by preparation of a phase, or by separation means.

The sixth step is to calculate the Density Difference: The Density Difference between the phases is calculated by subtracting the two values obtained for the Density of a Phase. Express the result as a positive number. When there are more than 2 phases present, three, or more than three, such Density Differences can be obtained by subtracting the values obtained in pairs.

Preferably, the Density Difference is less than 0.15 $g/cm^3$, more preferably, the Density Difference is less than 0.10 $g/cm^3$, even more preferably, the Density Difference is less than 0.08 $g/cm^3$, still more preferably, the Density Difference is less than 0.06 $g/cm^3$, still even more preferably, the Density Difference is less than 0.05 $g/cm^3$, most preferably, the Density Difference is less than 0.02 $g/cm^3$.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

The following examples described in Table 1 are comparative and non-limiting inventive examples of multiphase personal cleansing compositions.

TABLE 1

Multiphase Personal Cleansing Compositions

| | Comparative Example | Inventive Example 1 |
|---|---|---|
| Sodium Lauroamphoacetate (Cognis Chemical Corp.,) | 3.1 | 3.1 |
| Sodium Trideceth Sulfate (sulfated from Iconol TDA-3 (BASF Corp.) to >95% sulfate) | 5.3 | 5.3 |
| Sodium Lauryl Sulfate | 5.3 | 5.3 |
| Trideceth-3 (Iconal TDA-3 from BASF Corp.) | 1.3 | 1.3 |
| Sodium Chloride | 3.1 | 3.1 |
| Guar hydroxypropyltrimonium chloride (N-Hance 3196 Polymer) | 0.39 | 0.39 |
| PEG 90M (Polyox WSR301) | 0.10 | 0.10 |
| Xanthan gum (Keltrol 1000, Kelco Corp.) | 0.14 | 0.14 |
| Expancel (091 WE 40 d24, from Expancel Inc.) | — | 0.23 |
| Methyl chloro isothiazolinone and methyl isothiazolinone (Kathon CG, Rohm & Haas) | 0.00032 | 0.00032 |
| EDTA (Dissolvine NA 2x) | 0.10 | 0.10 |
| Sodium Benzoate | 0.13 | 0.13 |

TABLE 1-continued

Multiphase Personal Cleansing Compositions

| | Comparative Example | Inventive Example 1 |
|---|---|---|
| Citric Acid, titrate | pH = 5.7 ± 0.2 | pH = 5.7 ± 0.2 |
| Perfume | 1.0 | 1.0 |
| Petrolatum (from Quidesa, Mexico) | 35 | 35 |
| Water | Q.S. | Q.S. |
| Surfactant Phase Density (g/cm$^3$) | 1.04 | 0.90 |
| Benefit Phase Density (g/cm$^3$) | 0.88 | 0.88 |
| Density Difference (g/cm$^3$) | 0.16 | 0.02 |
| Rapid Stability Results (after 10 days @120 F.) | Creaming Unstable | No Creaming Stable |

The compositions described above can be prepared by conventional formulation and mixing techniques. Prepare the personal cleansing composition by first adding citric acid into water at 1:3 ratios to form a citric acid premix. Prepare a polymer premix by adding Polyox WSR301 and Xanthan Gum into Trideceth-3. Then, add the following ingredients into the main mixing vessel in the following sequence with agitation: water, N-Hance polymer, Expancel (Inventive Example 1). Pass the mixture (water, N-Hance, Expancel) through a mill to break up the Expancel agglomerate. Then add sodium lauroamphoacetate, sodium trideceth sulfate, sodium lauroamphoacetate, sodium lauryl sulfate, sodium chloride, sodium benzoate, and Disodium EDTA. Add citric acid premix to adjust pH to 5.7±0.2. Add the polymer premix, Kathon CG, and perfume into the main mixing vessel with continuous agitation. In a separate vessel, prepare the benefit phase by adding Petrolatum and heat to 190 F. Cool the benefit phase to 140 F with slow agitation. The surfactant phase and benefit phase are blended together through a Koch SMX 4 element mixer (¾" nominal) (available from Koch-Glitsch LP Mass Transfer Sales and Engineering, 9525 Kenwood Road, Suite 16-246, Cincinnati, Ohio 45242) to form a homogenous multiphase product.

The surfactant phase density of comparative Example has a density of about 1.04 g/cm$^3$ and the benefit phase density about 0.88 g/cm$^3$. The difference between the surfactant phase and benefit phase in the comparative Example is about 0.16 g/cm$^3$. The surfactant phase density of the inventive example has a density of about 0.90 g/cm$^3$ and the benefit phase density about 0.88 g/cm$^3$. The difference between the surfactant phase and the benefit phase in the inventive Example is about 0.02 g/cm$^3$. Both products are placed in a rapid stability testing for 10 days at 120 F. The comparative Example is not stable due to creaming of mineral oil to the surface. The inventive Example is stable without noticeable mineral oil creaming to the surface. The following examples further describe and demonstrate embodiments within the scope of the present invention. The examples are given solely for the purpose of illustration and are not to be construed as limitations of the present invention, as many variations thereof are possible without departing from the spirit and scope of the invention.

| | Examples of the Present Invention | | |
|---|---|---|---|
| | 2 | 3 | 4 |
| Ammonium Laureth-3 Sulfate (Procter & Gamble) | 3.0 | 3.0 | 3.0 |
| Sodium Lauroamphoacetate (Miranol L-32, Rhodia) | 16.7 | 16.7 | 16.7 |
| Ammonium Lauryl Sulfate (P&G) | 1.0 | 1.0 | 1.0 |
| Lauric Acid | 0.9 | 0.9 | 0.9 |
| Trihydroxystearin (Thixcin R) | 2.0 | 2.0 | 2.0 |
| Guar Hydroxypropyltrimonium Chloride (N-Hance 3196, Aqualon) | 0.5 | 0.5 | 0.5 |
| PEG 90M (Polyox WSR 301 from Dow Chemical) | 0.1 | 0.1 | 0.2 |
| Sodium Chloride | 0.3 | 0.3 | 0.3 |
| Sodium Benzoate | 0.25 | 0.25 | 0.25 |
| Disodium EDTA | 0.13 | 0.13 | 0.13 |
| Glydant | 0.37 | 0.37 | 0.37 |
| Citric Acid | 1.6 | 0.95 | 0.95 |
| Perfume | 0.5 | 0.5 | 0.5 |
| Expancel 091 DE 40 d30 from Expancel, Inc. | 0.3 | 0.3 | 0.3 |
| Petrolatum SuperWhite Protopet, WITCO | 10 | 15 | 20 |
| Water | Q.S. | Q.S. | Q.S. |
| Surfactant Phase Density (g/cm$^3$) | 0.93 | 0.93 | 0.92 |
| Benefit Phase Density (g/cm$^3$) | 0.88 | 0.88 | 0.88 |
| Density Difference (g/cm$^3$) | 0.05 | 0.05 | 0.04 |

The compositions described above can be prepared by conventional formulation and mixing techniques. First prepare a citric acid premix by adding citric acid in water at 1:3 ratio. Then, add the following ingredients into the main mixing vessel with agitation: surfactants, sodium chloride, sodium benzoate, disodium EDTA, lauric acid, Thixcin R, N-Hance 3196, Polyox WSR 301 and the rest of water. Heat the vessel with agitation until it reaches 190 F (88 C), then add the benefit phase, which is petrolatum. Mix for about 10 min. Cool the batch with slow agitation until it reaches 110° F. (43° C.). Add the following ingredients: Glydant, perfume, and Expancel. Keep mixing until homogeneous.

| | Examples of the Present Invention | | |
|---|---|---|---|
| | 5 | 6 | 7 |
| Miracare SLB-365 (Sodium Trideceth Sulfate, Sodium Lauroamphoacetate, CMEA, Rhodia) | 33.18 | 33.25 | 23.9 |
| Cationic guar, N-Hance 3196 from Aqualon | 0.56 | 0.49 | 0.35 |
| PEG 90M (Polyox WSR 301) | 0.16 | 0.14 | 0.05 |
| Sodium Chloride | 2.8 | 2.45 | 1.75 |
| Disodium EDTA | 0.1 | 0.1 | 0.1 |
| Sodium Benzoate | 0.16 | 0.16 | 0.16 |
| Glydant | 0.26 | 0.26 | 0.26 |
| Citric Acid | 0.4 | 0.4 | 0.4 |
| Perfume | 1.0 | 1.0 | 1.0 |
| Expancel 091 DE 40 d30, Expancel, Inc. | 0.32 | 0.28 | 0.2 |
| G2218 Petrolatum (from WITCO) | 18 | — | — |
| Petrolatum (Superwhite Protopet, WITCO) | — | 18 | 30 |
| Hydrobrite 1000 White Mineral Oil, WITCO | 12 | 12 | 20 |
| Water | Q.S. | Q.S. | Q.S. |
| pH adjustment (citric acid or NaOH) | (6.0) | (6.0) | (6.0) |
| Surfactant Phase Density (g/cm$^3$) | 0.90 | 0.91 | 0.91 |
| Benefit Phase Density (g/cm$^3$) | 0.88 | 0.88 | 0.88 |
| Density Difference (g/cm$^3$) | 0.02 | 0.03 | 0.03 |

Prepare the compositions described above by conventional formulation and mixing techniques. First prepare a citric acid premix by adding citric acid into water at 1:3 ratio. Then, add the following ingredients into the main mixing vessel in the following sequence with agitation: water, N-Hance 3196, Expancel, Polyox WSR 301, and Miracare SLB-365. Adjust the pH to 6.0 using citric acid premix. Then, add sodium chloride, disodium EDTA, sodium benzoate, Glydant, and perfume. In a separate vessel, prepare a benefit phase which is a hydrophobic phase, by preparing a lipid premix by adding Petrolatum into Mineral oil and heat to 190 F. Cool the lipid premix to 100 F and add into the main batch. Keep mixing until homogeneous.

|  | Examples of the Present Invention: | | |
|---|---|---|---|
|  | 8 | 9 | 10 |
| Sodium Trideceth Sulfate (Cedepal TD-407, Stepan) | 5.9 | 5.9 | 4 |
| Ammonium Lauryl Sulfate | 5.9 | 5.9 | 4 |
| Sodium Lauroamphoacetate (Miranol L-32) | 3.5 | 3.5 | 2.3 |
| Guar Hydroxypropyltrimonium Chloride (N-Hance 3196 Aqualon) | 0.45 | 0.45 | 0.3 |
| PEG 90M (Polyox WSR 301 from Dow Chemical) | 0.11 | 0.11 | 0.08 |
| Isosteareth-2 (Global Seven) | 0.75 | 0.75 | 0.5 |
| Xanthan Gum (Keltrol 1000, CP Kelco) | 0.15 | 0.15 | 0.1 |
| Sodium Chloride | 2.6 | 2.6 | 1.75 |
| Disodium EDTA | 0.1 | 0.1 | 0.1 |
| Sodium Benzoate | 0.16 | 0.16 | 0.16 |
| Glydant | 0.3 | 0.3 | 0.3 |
| Citric Acid | 0.3 | 0.3 | 0.3 |
| Perfume | 1.0 | 1.0 | 1.0 |
| Expancel 091 WE 40 d24 from Expancel, Inc. | 0.3 | 0.3 | 0.2 |
| G2218 Petrolatum (WITCO) | 18 | — | — |
| Petrolatum (Superwhite Protopet, WITCO) | — | 18 | 30 |
| Hydrobrite 1000 White Mineral Oil, WITCO | 12 | 12 | 20 |
| Water | Q.S. | Q.S. | Q.S. |
| pH adjust to (use citric acid or NaOH) | 6.0 | 6.0 | 6.0 |
| Surfactant Phase Density (g/cm$^3$) | 0.88 | 0.88 | 0.89 |
| Benefit Phase Density (g/cm$^3$) | 0.88 | 0.88 | 0.88 |
| Density Difference (g/cm$^3$) | 0.00 | 0.00 | 0.01 |

Prepare the compositions described above by conventional formulation and mixing techniques. First prepare a citric acid premix by adding citric acid into water at 1:3 ratio and a polymer premix by adding Polyox WSR 301 and Keltrol 1000 to isosteareth-2. Then, add the following ingredients into the main mixing vessel with agitation: water, N-Hance 3196, sodium trideceth sulfate, sodium lauroamphoacetate, citric acid premix, ammonium lauryl sulfate. Then add polymer premix (Polyox and Keltrol 1000 in isosteareth-2). Add sodium chloride, disodium EDTA, sodium benzoate, Glydant, and perfume. In a separate vessel, prepare a benefit phase which is a hydrophobic phase, by preparing a lipid premix by adding Petrolatum into Mineral oil and heat to 190 F. Cool the lipid premix to 100 F and then add into the main batch. Adjust pH to 6.0. Keep agitation until homogeneous.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A mild, multiphase personal cleansing composition comprising:
a cleansing phase comprising a density modifier, an electrolyte, and a structured surfactant component that provides a Total Lather Volume of at least about 600 ml, the structured surfactant component comprising at least one surfactant; and,
a benefit phase substantially free of surfactants and substantially anhydrous, the benefit phase comprising a benefit component,
wherein the density of the cleansing phase differs from the density of the benefit phase by less than 0.15 g/cm$^3$.

2. The mild, multi-phase personal cleansing composition according to claim 1, wherein said density modifier comprises a low density microsphere.

3. The mild, multi-phase personal cleansing composition according to claim 2 wherein said low density microsphere comprises a particle having a density lower than 0.7 g/cm$^3$.

4. The mild, multi-phase personal cleansing composition according to claim 2 wherein said low density microsphere is selected from the group consisting of inorganic material, organic material and mixtures thereof.

5. The mild, multiphase cleansing composition of claim 1, wherein said structured surfactant component provides a Total Lather Volume of at least about 800 ml.

6. The mild, multiphase cleansing composition of claim 1, wherein said structured surfactant component provides a Yield Point of greater than about 0.5 Pascal.

7. The mild, multiphase cleansing composition of claim 1, comprising from about 1% to about 95%, by weight of the composition, of said structured surfactant component.

8. The mild, multiphase cleansing composition of claim 1, wherein said surfactant is selected from the group consisting of anionic surfactant, nonionic surfactant, zwitterionic surfactant, cationic surfactant, amphoteric surfactant, soap, and mixtures thereof.

9. The mild, multiphase cleansing composition of claim 8 wherein said anionic surfactant is selected from the group consisting of alkyl ether sulfates, alkyl sulfonates and mixtures thereof.

10. The mild, multiphase cleansing composition of claim 8, wherein said amphoteric surfactant is selected from the group consisting of sodium lauroamphoacetate, sodium cocoamphoactetate, disodium lauroamphoacetate, and disodium cocodiamphoacetate, and mixtures thereof.

11. The mild, multiphase cleansing composition of claim 8, wherein said nonionic surfactant is selected from the group consisting of glyceryl monohydroxystearate, steareth-2, propylene glycol stearate, sorbitan monostearate, glyceryl stearate, laureth-2, and mixtures thereof.

12. The mild, multiphase cleansing composition of claim 8, comprising from about 0.1% to about 50%, by weight of said structured surfactant component, of said nonionic surfactant.

13. The mild, multiphase cleansing composition of claim 12, wherein said nonionic surfactant has an HLB of from about 1.5 to about 15.0.

14. The mild, multiphase cleansing composition of claim 1, wherein said composition comprises a structured domain wherein said structured domain is an opaque structured domain.

15. The mild, multiphase cleansing composition of claim 14, wherein said opaque structured domain is a lamellar phase.

16. The mild, multiphase cleansing composition of claim 1, wherein said benefit component is selected from the group consisting of lipids, hydrocarbons, fats, oils, emollients, hydrophobic plant extracts, fatty acids, essential oils, silicone materials, vitamins and derivatives thereof; sunscreens; preservatives; anti-acne medicaments; antioxidants; chelators; sequestrants; skin sensates, and mixtures thereof.

17. The mild, multiphase cleansing composition of claim 1, wherein said composition comprises at least 30% benefit component wherein said benefit component is selected from the group consisting of lipids, hydrocarbons, fats, oils, emollients, hydrophobic plant extracts, fatty acids, essential oils, silicone materials, vitamins and derivatives thereof; and mixtures thereof.

18. A mild, multiphase cleansing composition comprising:
   a opaque, lamellar, cleansing phase comprising a density modifier, an electrolyte, and a structured surfactant component that provides a Total Lather Volume of at least about 600 ml; and,
   a benefit phase substantially free of surfactants and substantially anhydrous, the benefit phase comprising a benefit component;
   wherein the density of the cleansing phase differs from the density of the benefit phase by less than 0.15 g/cm$^3$.

19. The mild, multiphase cleansing composition of claim 18, wherein said structured surfactant component is selected from the group consisting of an anionic surfactant, an nonionic surfactant, an zwitterionic surfactant, an cationic surfactant, an amphoteric surfactant, soap, and mixtures thereof.

20. The mild, multiphase cleansing composition of claim 19, wherein said nonionic surfactant has an HLB of from about 3 to about 10.

21. The mild, multiphase cleansing composition of claim 18, wherein said benefit component is selected from the group consisting of lipids, hydrocarbons, fats, oils, emollients, hydrophobic plant extracts, fatty acids, essential oils, silicone materials; vitamins and derivatives thereof; sunscreens; preservatives; anti-acne medicaments; antioxidants; chelators and sequestrants; skin sensates, and mixtures thereof.

22. A mild, multiphase personal cleansing composition comprising:
   a cleansing phase comprising a density modifier, an electrolyte, and a structured surfactant component that provides a Total Lather Volume of at least about 600 ml, the structured surfactant component comprising at least one surfactant;
   a benefit phase substantially free of surfactants and substantially anhydrous, the benefit phase comprising a benefit component,
   said composition having a density of less than about 0.97 g/cm$^3$.

* * * * *